US009215788B2

United States Patent
Karni et al.

(10) Patent No.: US 9,215,788 B2
(45) Date of Patent: Dec. 15, 2015

(54) SYSTEM AND METHOD FOR TREATING BIOLOGICAL TISSUE WITH A PLASMA GAS DISCHARGE

(75) Inventors: Ziv Karni, Kfar Shmaryahu (IL); Alexander Britva, Migdal Haemek (IL)

(73) Assignee: ALMA LASERS LTD.

( * ) Notice: Subject to any disclaimer, the term of this patent is extended or adjusted under 35 U.S.C. 154(b) by 2521 days.

(21) Appl. No.: 11/333,308

(22) Filed: Jan. 18, 2006

(65) Prior Publication Data

US 2006/0189976 A1   Aug. 24, 2006

Related U.S. Application Data

(60) Provisional application No. 60/644,037, filed on Jan. 18, 2005.

(51) Int. Cl.
A61B 18/12 (2006.01)
H05H 1/24 (2006.01)
(Continued)

(52) U.S. Cl.
CPC ............... *H05H 1/24* (2013.01); *A61B 18/042* (2013.01); *A61B 18/20* (2013.01); *A61B 2018/00452* (2013.01); *A61B 2018/122* (2013.01)

(58) Field of Classification Search
CPC .................. A61B 18/042; A61B 2018/00452; A61B 2018/1213; A61B 2018/122; H05H 1/24
USPC .................................................. 606/32, 34, 41
See application file for complete search history.

(56) References Cited

U.S. PATENT DOCUMENTS 3,903,891 A * 9/1975 Brayshaw ...................... 606/27
4,140,130 A   2/1979 Storm (Continued)

FOREIGN PATENT DOCUMENTS

CA   1228401   10/1987
EP   1090598    9/2005

(Continued)

OTHER PUBLICATIONS

EPO Office Action for EPO Application "EP1810626," (parallel case in EPO) published Jul. 23, 2010.

(Continued)

*Primary Examiner* — Michael Peffley
*Assistant Examiner* — Samantha Good

(57) ABSTRACT

Devices and methods for treating biological tissue using a plasma gas-discharge are disclosed herein. An electrode for igniting a gas flow to form a plasma gas-discharge, wherein the electrode is configured within the device such that upon encountering a surface of the biological tissue by the electrode, a path of current from the electrode to the surface of the biological tissue is formed, thereby igniting the gas flow and forming the plasma gas-discharge. In some embodiments, electromagnetic interactions between the treated biological tissue and the plasma gas discharge traversing the electromagnetic interaction gap shape the profile of the plasma gas discharge. According to some embodiments, the device includes an electrode for igniting gas of the gas flow, and electromagnetic interactions between the electrode and the skin determine, at least in part, the electromagnetic interactions that shape the profile of the plasma gas discharge. In some embodiments, the device further includes a housing for providing support for the electrode, wherein the electrode is disposed relative to the housing such that the electrode is substantially electrically unshielded by the housing, and the electrode is positioned to electromagnetically interact with a surface of the biological tissue to shape, at least in part, the plasma profile. According to some embodiments, the presently disclosed device includes a dual-purpose nozzle-electrode for gas delivery and for igniting the gas flow. A method of transdermal ion delivery of a plasma flux to biological tissue as a means of treating the biological tissue is also provided.

7 Claims, 8 Drawing Sheets

(51) Int. Cl.
  *A61B 18/04* (2006.01)
  *A61B 18/20* (2006.01)
  *A61B 18/00* (2006.01)

(56) References Cited

U.S. PATENT DOCUMENTS

| | | | |
|---|---|---|---|
| 4,210,152 A | | 7/1980 | Berry |
| 4,674,481 A | | 6/1987 | Boddie |
| 4,798,215 A | | 1/1989 | Turner |
| 4,901,719 A | * | 2/1990 | Trenconsky et al. ............ 606/49 |
| 4,901,720 A | | 2/1990 | Bertrand |
| 5,038,780 A | | 8/1991 | Boetzkes |
| 5,097,844 A | | 3/1992 | Turner |
| 5,458,596 A | | 10/1995 | Lax |
| 5,484,432 A | | 1/1996 | Sand |
| 5,507,790 A | | 4/1996 | Weiss |
| 5,669,907 A | * | 9/1997 | Platt et al. ....................... 606/48 |
| 5,755,753 A | | 5/1998 | Knowlton |
| 5,919,219 A | | 7/1999 | Knowlton |
| 6,013,075 A | * | 1/2000 | Avramenko et al. ............ 606/40 |
| 6,099,523 A | | 8/2000 | Kim et al. |
| 6,105,581 A | | 8/2000 | Eggers et al. |
| 6,149,620 A | | 11/2000 | Baker |
| 6,203,850 B1 | | 3/2001 | Nomura |
| 6,228,078 B1 | | 5/2001 | Eggers |
| 6,387,088 B1 | * | 5/2002 | Shattuck et al. .................. 606/2 |
| 6,518,538 B2 | | 2/2003 | Bernabei |
| 6,595,990 B1 | | 7/2003 | Weinstein |
| 6,629,974 B2 | | 10/2003 | Penny |
| 6,662,054 B2 | | 12/2003 | Kreindel |
| 6,723,091 B2 | | 4/2004 | Goble |
| 6,780,178 B2 | | 8/2004 | Palanker |
| 6,958,063 B1 | * | 10/2005 | Soll et al. ........................ 606/41 |
| 7,182,762 B2 | * | 2/2007 | Bortkiewicz .................... 606/41 |
| 7,608,839 B2 | * | 10/2009 | Coulombe et al. ............ 250/426 |
| 2001/0034519 A1 | | 10/2001 | Goble |
| 2002/0043520 A1 | | 4/2002 | Bernabei |
| 2003/0130653 A1 | * | 7/2003 | Sixto et al. ...................... 606/45 |
| 2004/0002705 A1 | | 1/2004 | Knowlton |
| 2004/0030332 A1 | | 2/2004 | Knowlton |
| 2004/0044342 A1 | | 3/2004 | Mackay |
| 2004/0116918 A1 | | 6/2004 | Konesky |
| 2004/0186470 A1 | * | 9/2004 | Goble et al. ..................... 606/41 |
| 2005/0173383 A1 | | 8/2005 | Coccio et al. |
| 2006/0084158 A1 | | 4/2006 | Viol |

FOREIGN PATENT DOCUMENTS

| | | |
|---|---|---|
| GB | 1222243 | 2/1971 |
| JP | 02201315 | 3/1992 |
| JP | 4089068 | 3/1992 |
| JP | 0594961 | 10/1994 |
| JP | 6285175 | 10/1994 |
| WO | WO0230308 | 4/2002 |
| WO | WO/2004/105810 | 9/2004 |
| WO | WO2004/047659 | 10/2004 |

OTHER PUBLICATIONS

USPTO Office Action for Related U.S. Appl. No. 12/488,566 (a continuation of the parent case of the present application), mailed on Jul. 2, 2010.

PCT Search Report (ISR) of PCT/IL2006/000069 (the PCT of the present application), Search Report published on Sep. 26, 2007.

PCT Report of Patentability (IPR)of PCT/IL2006/000069 (the PCT of the present application), Patentability Report published on Sep. 26, 2007.

Christopher E.M. Griffiths, et aL"RestoratIon of Collagen Formation in Photodamaged Human Skin by Tretinoin (Retlnoic Acid)," New England J. Med., 329: 530-535 (Aug. 19, 1993).

Haria Ghersetich, "Ultrastructural Study of Hyaluronic Acid Before and After the Use of a Pulsed Electromagnetic Field, Electrorydesis, in the Treatment of Wrinkles," Int'l J. DermatoL, 33:661-663 (1994).

EP1810626 File Wrapper for Parallel Case in EPO, downloaded on Jul. 4, 2010.

Israel Office Action for Parallel Case in Israel IL180519, issued on Jan. 24, 2010.

* cited by examiner

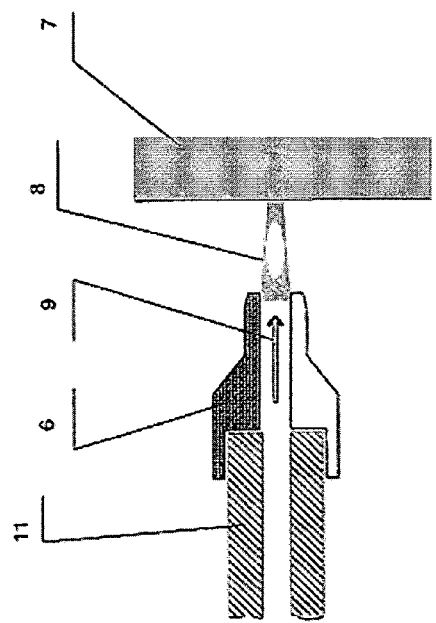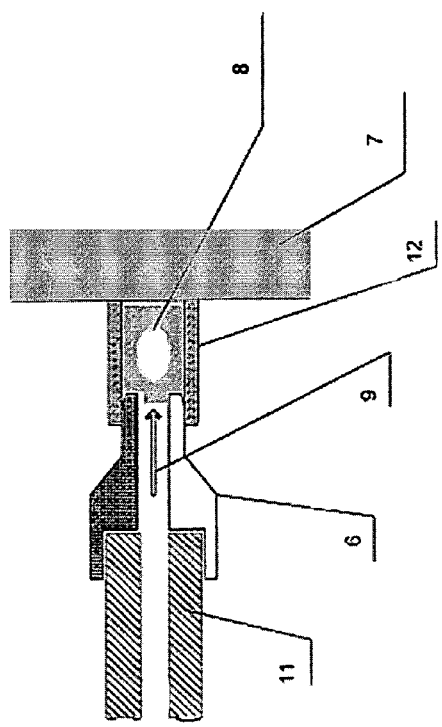

SYSTEM AND METHOD FOR TREATING BIOLOGICAL TISSUE WITH A PLASMA GAS DISCHARGE

CROSS-REFERENCE TO RELATED APPLICATIONS

This application claims the benefit of U.S. Provisional Patent Application No. 60/644,037, filed Jan. 18, 2005, the disclosure of which is incorporated by reference in its entirety.

FIELD AND BACKGROUND OF THE INVENTION

The exemplary system relates to an improved system and method for treating biological tissue, and more specifically the skin layer, via an RF plasma gas-discharge at atmospheric pressures where the gas nozzle-electrode which serves as an RF-energy coupling antenna that functions in combination with an adjacent biological tissue acting as a second virtual electrode. Control of the gas discharge, or plasma, is effected in multiple ways including: gas nozzle-electrode configuration, nature of gas(es), and gas flow parameters. This system and method enables a broader range of skin treatment, resurfacing, and revitalization techniques to be applied that can be optimized to the needs of the treatment. Specifically, conditions for low temperature ablation of the skin layer minimizing thermal damage, controlled and localized heating of the skin layer, and transdermal ion delivery are achievable.

Skin treatment, such as skin resurfacing or revitalization, involves removal and/or modification of the outer and near-surface skin layer depending on the treatment needs. Skin treatments can be applied to needs such as wrinkle removal, pore tightening, skin smoothing, muscle lifting, collagen stimulation, lentigo (e.g. tattoo, scar, lesion, blemish, and hyper-pigmentation) removal, and hair removal and growth suppression. Previously proposed methods for skin treatment predominantly involve topical treatments which are either chemical in nature, such as creams or ointments, mechanical (i.e. abrasive), or a combination of both. These techniques have not demonstrated clinical efficacy in reducing skin treatment problems over a long-term period and preventing problem reappearance. In addition, chemical and mechanical "peeling" can have damaging effects on the problem skin area and/or surrounding tissue.

In addition, newer methods have been proposed for skin treatment utilizing laser, RF plasma, and LED light energy to interact with the skin layer. Each of the methods poses advantages and disadvantages to the application.

Previously available alternatives are characterized by disadvantages which are obviated by the exemplary system. Some of the problems associated with these types of techniques include: limited operating conditions, excessive skin heating and/or burning, incomplete blemish removal, extended healing periods, rashes, and other skin irritations and/or complications.

One example of a prior art system is disclosed in U.S. Pat. No. 6,105,581 assigned to ArthoCare Corporation. This patent teaches using an electrically-conductive solution, such as a salt solution, in contact with the skin and an electrosurgical probe. The application of RF-energy impulses to the probe produces a plasma in the solution causing cells on the surface of the skin and within the spine to be ablated. The solution removes heat from the plasma maintaining a low temperature which mitigates the problem of excessive skin heating associated with laser resurfacing. This technique has been referred to in the art sometimes as Coblation® technology. However, teachings of this patent have, as an inherent disadvantage, inadequate control of skin treatment region due to plasma "hot spots" being produced in various areas of the applied solution, and limited application due to the need for contact of the probe with the skin treatment region.

Another example of a prior art system is disclosed in U.S. Pat. No. 6,518,538 assigned to Mattioli Engineering Ltd. This patent teaches using an RF plasma gas-discharge to heat and selectively damage the skin layer. The skin layer to be treated is sealed to the probe and a vacuum is produced within the probe. An RF energy-coupled electrode and helium gas are introduced into the probe, whereby the plasma is produced. However, teachings of this patent have, as an inherent disadvantage, the limitation of operating under vacuum conditions, and the limitation of skin treatment regions suitable to probe position and obtaining suitable vacuum pressures without extraneous, adverse results.

Another example of a prior art system is disclosed in U.S. Pat. Nos. 6,629,974 and 6,723,091 assigned to Gyrus Medical Limited. This system uses an RF plasma gas-discharge of nitrogen to deliver its energy in a 6 mm spot to the treatment region. One of its major advantages over laser-based systems is that it does not depend on an intermediate chromophore to convert the RF energy into heat. Thus, heat dissipation is controlled and uniform. Furthermore, multiple passes of the plasma flame over the treatment area did not result in additive thermal damage as in laser-based systems. However, this system has, as an inherent disadvantage, the limitation of operating with only a small active plasma region for skin treatment. This is due, in part, to the fact that the plasma is ignited inside the housing of the device. This precludes any beneficial electromagnetic interactions between the electrode and the skin surface to assist in shaping the plasma profile.

Thus, there is a widely-recognized need for, and it would be highly advantageous to have, an improved system and method for heating biological tissue via an RF plasma gas-discharge devoid of the above limitation(s).

SUMMARY OF THE INVENTION

The aforementioned needs are satisfied by several aspects of the exemplary system.

It is now disclosed for the first time a device for treating biological tissue. The presently disclosed device includes an electrode for igniting a gas flow to form a plasma gas-discharge, wherein the electrode is configured within the device such that upon encountering a surface of the biological tissue by the electrode, a path of current from the electrode to the surface of the biological tissue is formed, thereby igniting the gas flow and forming the plasma gas-discharge.

According to some embodiments, the electrode is a nozzle-electrode including a nozzle portion adapted to receive the gas flow.

According to some embodiments, said nozzle-electrode is adapted to ignite the gas flow such that the plasma gas-discharge is formed, at least in part, outside of the nozzle portion.

According to some embodiments, the device operates at or above atmospheric pressure.

According to some embodiments, the plasma gas-discharge produced by the device is effective to treat the biological tissue by ablating the biological tissue.

According to some embodiments, the plasma gas-discharge produced by the device is effective to treat the biological tissue by cutting the biological tissue.

According to some embodiments, the plasma gas-discharge produced by the device is effective to treat the biological tissue by transdermal ion delivery to the biological tissue.

According to some embodiments, the plasma gas-discharge produced by the device is effective to treat the biological tissue by heating the biological tissue.

According to some embodiments, the plasma gas-discharge produced by the device is effective to treat the biological tissue by bio-photostimulation of the biological tissue.

According to some embodiments, the plasma gas-discharge produced by the device is effective to treat the biological tissue by chemically reacting the plasma gas-discharge with the biological tissue.

According to some embodiments, the gas flow is a diffusive gas flow.

According to some embodiments, the device further includes a gas source for producing the gas flow, the gas source provides at least one gas selected from the group consisting of: helium, argon, neon, xenon, krypton, molecular oxygen ($O_2$), molecular nitrogen ($N_2$), oxides of nitrogen, oxides of carbon, water vapor, a volatile organic gas, and a volatile inorganic gas.

According to some embodiments, the electrode is composed of at least one metal selected from the group consisting of: aluminum, silver, gold, copper, and alloys thereof.

According to some embodiments, the device further includes a dielectric barrier associated with a surface of the electrode for reducing an electrical conductivity of the surface of the electrode, thereby impeding transmission of a conductive current to the surface of biological tissue.

According to some embodiments, the electrode is dimensioned to form a torch-type profile from the plasma gas-discharge.

According to some embodiments, the electrode has a dielectric cylindrical cavity attachment and is dimensioned to form the plasma gas-discharge such that the plasma gas-discharge substantially occupies the total cavity of the dielectric cylindrical cavity attachment.

According to some embodiments, the electrode is dimensioned to form the plasma gas-discharge with a very low current density and a high discharge cross-section.

According to some embodiments, the electrode is dimensioned to form a narrow flame-tongue (plasmatron) profile from the plasma gas-discharge.

According to some embodiments, the electrode is dimensioned and positioned to interact with the surface of the biological tissue in a way that the surface of the biological tissue is a non-equipotential surface, allowing for simultaneous heating of the biological tissue and maintaining the plasma gas-discharge.

According to some embodiments, the electrode is dimensioned with a bowl profile and positioned to directly contact the biological tissue in a way that the surface of the biological tissue is a non-equipotential surface, enabling the plasma gas-discharge to substantially fill interior volume of the electrode.

According to some embodiments, the electrode has a dielectric cylindrical cavity attachment and is dimensioned with a spherical profile for directly contacting the biological tissue in a way that the surface of the biological tissue is a non-equipotential surface, providing the plasma gas-discharge with a ring-type profile.

According to some embodiments, the electrode has a dielectric cylindrical conduit attachment which extends into interior of the electrode directly contacting the biological tissue, thereby igniting the plasma gas-discharge inside the dielectric cylindrical conduit attachment, the plasma gas-discharge is transported to the biological tissue by the gas flow.

According to some embodiments, the device further includes at least one additional component selected from the group consisting of: a laser beam, an ultrasonic transducer, a UV light source, and a flash lamp, thereby additionally treating the biological tissue.

According to some embodiments, the electrode serves as an antenna for the plasma gas-discharge and affects parameters of the gas flow for the plasma gas-discharge.

According to some embodiments, the device further includes a nozzle for gas delivery, the nozzle suitable for producing a strong decrease in temperature of the gas (adiabatic expansion).

According to some embodiments, the device further includes a nozzle for gas delivery, the nozzle suitable for producing a laminar gas flow.

According to some embodiments, the device further includes a nozzle for gas delivery, the nozzle suitable for producing a turbulent gas flow.

According to some embodiments, the device further includes a nozzle for gas delivery, the nozzle suitable for producing a gas flow effective for transdermal ion delivery.

According to some embodiments, the plasma-gas discharge is produced by an RF power generator (amplifier) capable of producing an output RF power sufficient to ignite and sustain the plasma gas-discharge.

According to some embodiments, the device further includes an electrode control for regulating a power characteristic of the electrode.

According to some embodiments, the electrode control includes an RF power source for providing RF power to the electrode.

According to some embodiments, the electrode control includes a phase shifter capable of shifting a phase of directed traveling waves.

According to some embodiments, the electrode control includes an impedance-matching network (IMN), the IMN capable of converting an aggregate impedance of the device including the plasma gas-discharge, the electrode, and the biological tissue (DET—discharge-electrode-tissue) from a nominal value to a corrected value.

According to some embodiments, the electrode control includes an RF resonator capable of cyclically accumulating and releasing a desired amount of energy.

According to some embodiments, the electrode control includes: (a) an RF power generator (amplifier) capable of producing an output RF power sufficient to ignite and sustain the plasma gas-discharge, (b) a pulse-width modulation (PWM) controller, the PWM controller capable of causing the RF power generator to deliver the output RF power in pulses of a predetermined duration and amplitude with a desired frequency, (c) a phase shifter capable of shifting a phase of directed traveling waves, the phase shifter capable of shifting a phase of directed traveling waves of the output power via a phase jump in order to facilitate both an ignition stage and an operation stage of the plasma gas-discharge, (d) an impedance-matching network (IMN), the IMN capable of converting an aggregate impedance of the device including the plasma gas-discharge, the electrode, and the biological tissue (DET—discharge-electrode-tissue) from a nominal value to a corrected value for both the ignition stage and the operation stage, the corrected value matching to a characteristic impedance of the RF power generator and the phase shifter so that the output traveling wave may sustain the plasma gas-discharge without being converted to a standing wave, and (e) an RF resonator connected to the electrode, the RF resonator capable of cyclically accumulating and releasing a desired amount of energy for the operation stage, the RF resonator further capable of concentrating the desired amount of energy for the ignition stage.

According to some embodiments, the dielectric barrier is supplied as a dielectric coating on the electrode.

According to some embodiments, the electrode is constructed primarily of aluminum and the dielectric barrier is supplied as an alumina coating.

It is now disclosed for the first time a device for treating biological tissue using a shaped plasma profile formed from a gas flow. The presently disclosed device includes: (a) an electrode for igniting the gas flow to produce a plasma gas-discharge, and (b) a housing for providing support for said electrode, wherein said electrode is disposed relative to said housing such that said electrode is substantially electrically unshielded by said housing, and said electrode is positioned to electromagnetically interact with a surface of the biological tissue to shape, at least in part, the plasma profile.

According to some embodiments, the device is configured such that the plasma-gas discharge is substantially located outside the housing.

According to some embodiments, the electrode is attached to the housing via an electrode holder, the electrode holder serves both to position the electrode relative to the housing and to deliver gas of the gas flow to the electrode.

According to some embodiments, at least a portion of the electrode is exposed on the housing to allow direct contact with the surface of the biological tissue.

According to some embodiments, the disposition of the electrode is adjustable relative to the housing to allow movement along the surface of the biological tissue as a means of controlling a region of treatment of the biological tissue.

It is now disclosed for the first time a device for treating biological tissue. The presently disclosed device includes: (a) an RF power generator (amplifier) capable of producing an output RF power sufficient to ignite and sustain a plasma gas-discharge, (b) a pulse-width modulation (PWM) controller, the PWM controller capable of causing the RF power generator to deliver the output RF power in pulses of a predetermined duration and amplitude with a desired frequency, (c) a phase shifter capable of shifting a phase of directed traveling waves, the phase shifter capable of shifting a phase of directed traveling waves of the output power via a phase jump in order to facilitate both an ignition stage and an operation stage of the plasma gas-discharge, (d) an impedance-matching network (IMN), the IMN capable of converting an aggregate impedance of the device including the plasma gas-discharge, the electrode, and the biological tissue (DET—discharge-electrode-tissue) from a nominal value to a corrected value for both the ignition stage and the operation stage, the corrected value matching to a characteristic impedance of the RF power generator and the phase shifter so that the output traveling wave may sustain the plasma gas-discharge without being converted to a standing wave, and (e) an RF resonator connected to the electrode, the RF resonator capable of cyclically accumulating and releasing a desired amount of energy for the operation stage, the RF resonator further capable of concentrating the desired amount of energy for the ignition stage.

According to some embodiments, coupled power is delivered from the RF power generator.

According to some embodiments, the output RF power delivered to the plasma gas-discharge is coupled in continuous or pulsing mode.

According to some embodiments, the phase shifter includes a trombone type.

According to some embodiments, the phase shifter is at least partially constructed of coaxial cable.

According to some embodiments, a phase shift provided by the phase shifter is variable.

According to some embodiments, the IMN includes a fixed structure characterized by a shape selected from the group consisting of: L-shaped, T-shaped, and π-shaped structure.

According to some embodiments, the IMN includes a broadband impedance transformer.

According to some embodiments, the IMN is variable.

According to some embodiments, the device further includes: (f) a feeding cable, the feeding cable connecting the electrode and the RF resonator with the IMN.

According to some embodiments, the feeding cable has a resonance length defined by n*?/2 length, where ? is a wavelength of the output RF power in material of the feeding cable and n is a whole number.

It is now disclosed for the first time a device for treating biological tissue using a shaped plasma profile formed from a gas flow. The presently disclosed device includes: (a) a nozzle-electrode for gas delivery and for igniting the gas flow to produce a plasma gas-discharge, and (b) a housing providing support for said nozzle-electrode, wherein said nozzle-electrode is disposed relative to said housing such that said nozzle-electrode is substantially electrically unshielded by said housing, and said nozzle-electrode is positioned to electromagnetically interact with a surface of the biological tissue to shape, at least in part, the plasma profile.

It is now disclosed for the first time a method for treating biological tissue. The presently disclosed method includes: (a) supplying a gas flow to an electrode, (b) upon bringing a surface of the biological tissue and an electrode into proximity with each other such that the electrode and the biological tissue are substantially electrically unshielded from each other, igniting the gas flow to form a plasma gas-discharge, and (c) subjecting the surface of the biological tissue to the plasma-gas discharge, thereby treating the biological tissue.

According to some embodiments, the biological tissue is treated by ablating the biological tissue.

According to some embodiments, the biological tissue is treated by cutting the biological tissue.

According to some embodiments, the biological tissue is treated by transdermally delivering ions to the biological tissue.

According to some embodiments, the biological tissue is treated by heating the biological tissue.

According to some embodiments, the biological tissue is treated by bio-photostimulating the biological tissue.

According to some embodiments, the biological tissue is treated by chemically reacting the plasma gas-discharge with the biological tissue.

According to some embodiments, the biological tissue is electrically grounded in order to interact with the plasma gas-discharge.

According to some embodiments, the biological tissue is electrically floating in order to interact with the plasma gas-discharge.

According to some embodiments, the plasma gas-discharge operates at or above atmospheric pressure.

According to some embodiments, the method further includes: (d) producing an output RF power sufficient to ignite and sustain the plasma gas-discharge by means of an RF power generator (amplifier), (e) causing the RF power generator to deliver the output RF power in pulses of a predetermined duration and amplitude with a desired frequency by means of by means of a pulse-width modulation (PWM) controller, (f) shifting a phase of directed traveling waves of the output power via a phase jump in order to facilitate both an ignition stage and an operation stage of the plasma gas-discharge by means of a phase shifter, (g) converting an aggregate impedance including the plasma gas-discharge, the electrode, and the biological tissue (DET—discharge-electrode-tissue) from a nominal value to a corrected value for both the ignition stage and the operation stage, the corrected value matching to a characteristic impedance of the RF power generator and the phase shifter so that the output traveling wave may sustain the plasma gas-discharge without being converted to a standing wave by means of an impedance-matching network (IMN), and (h) cyclically accumulating and releasing a desired amount of energy for the operation stage, the RF resonator further capable of concentrating the desired amount of energy for the ignition stage by means of an RF resonator connected to the electrode.

According to some embodiments, the step of igniting the gas flow from the electrode includes igniting the gas flow from an electrode attached to the device via an electrode holder, the electrode holder also serves to deliver a gas to the electrode.

According to some embodiments, the step of igniting the gas flow from the electrode includes igniting the gas flow from an electrode located in direct contact with the surface of the biological tissue.

According to some embodiments, the step of igniting the gas flow from the electrode includes igniting the gas flow from an electrode movable on the surface of the biological tissue as a means of altering a location of treating the biological tissue.

According to some embodiments, the method further includes: (d) positioning a dielectric barrier between the electrode and the surface of the biological tissue, the dielectric barrier impeding transmission of a conductive current.

According to some embodiments, the step of igniting the gas flow from the electrode includes igniting the gas flow from an electrode exposed to atmosphere and having a dimension and a profile for producing the plasma gas-discharge that has a torch-type profile.

According to some embodiments, the step of igniting the gas flow from the electrode includes igniting the gas flow from an electrode having a dielectric cylindrical cavity attachment and having a dimension and a profile for producing the plasma gas-discharge that occupies the total cavity of the dielectric cylindrical cavity attachment.

According to some embodiments, the step of igniting the gas flow from the electrode includes igniting the gas flow from an electrode having a dimension and a profile for producing the plasma gas-discharge with a very low current density and a high discharge cross-section.

According to some embodiments, the step of igniting the gas flow from the electrode includes igniting the gas flow from an electrode having a dimension and a profile for producing the plasma gas-discharge with a narrow flame-tongue (plasmatron) profile.

According to some embodiments, the step of igniting the gas flow from the electrode includes igniting the gas flow from an electrode having a dimension and a profile for interacting with the surface of the biological tissue, in a way that the surface of the biological tissue is a non-equipotential surface, allowing for simultaneous heating of the biological tissue and maintaining of the plasma gas-discharge.

According to some embodiments, the step of igniting the gas flow from the electrode includes igniting the gas flow from an electrode having a bowl profile for directly contacting the biological tissue in a way that the surface of the biological tissue is a non-equipotential surface, enabling the plasma gas-discharge to fill interior volume of the nozzle electrode.

According to some embodiments, the step of igniting the gas flow from the electrode includes igniting the gas flow from an electrode having a dielectric cylindrical cavity attachment and having a spherical profile for partially directly contacting the biological tissue in a way that the surface of the biological tissue is a non-equipotential surface, providing the plasma gas-discharge with a ring-type profile.

According to some embodiments, the step of igniting the gas flow from the electrode includes igniting the gas flow from an electrode having a dielectric cylindrical conduit attachment which extends into interior of the electrode directly contacting the biological tissue which yields a plasma gas-discharge ignited inside the dielectric cylindrical conduit attachment, the plasma gas-discharge is transported to the biological tissue by the gas flow.

According to some embodiments, the method further includes: (d) employing at least one additional component selected from the group consisting of: a laser beam, an ultrasonic transducer, a UV light source, and a flash lamp to additionally treat the biological tissue.

According to some embodiments, the step of providing a gas flow includes providing a gas flow having flow characteristics suitable to produce a strong decrease in temperature of the gas (adiabatic expansion).

According to some embodiments, the step of providing a gas flow includes providing a gas flow having flow characteristics suitable to produce a laminar gas flow characteristic.

According to some embodiments, the step of providing a gas flow includes providing a gas flow having flow characteristics suitable to produce a turbulent gas flow characteristic.

According to some embodiments, the step of providing a gas flow includes providing a gas flow having flow characteristics suitable to facilitate transdermal ion delivery.

According to some embodiments, the steps of (a) through (c) are performed in the order listed.

It is now disclosed for the first time a method for treating biological tissue. The presently disclosed method includes: (a) supplying a gas flow to an electrode, (b) allowing a path of current to form from the electrode to a surface of the biological tissue to concomitantly ignite the gas flow to form a plasma gas discharge, and (c) subjecting the surface of the biological tissue to the plasma-gas discharge, thereby treating the biological tissue It is now disclosed for the first time a method for treating biological tissue using a plasma gas-discharge. The presently disclosed method includes: (a) producing an output RF power sufficient to ignite and sustain the plasma gas-discharge by means of an RF power generator (amplifier), (b) causing the RF power generator to deliver the output RF power in pulses of a predetermined duration and amplitude with a desired frequency by means of by means of a pulse-width modulation (PWM) controller, (c) shifting a phase of directed traveling waves of the output power via a phase jump in order to facilitate both an ignition stage and an operation stage of the plasma gas-discharge by means of a phase shifter, (d) converting an aggregate impedance including the plasma gas-discharge, the electrode, and the biological tissue (DET—discharge-electrode-tissue) from a nominal value to a corrected value for both the ignition stage and the operation stage, the corrected value matching to a characteristic impedance of the RF power generator and the phase shifter so that the output traveling wave may sustain the plasma gas-discharge without being converted to a standing wave by means of an impedance-matching network (IMN), and (e) cyclically accumulating and releasing a desired amount of energy for the operation stage, the RF resonator further capable of concentrating the desired amount of energy for the ignition stage by means of an RF resonator connected to the electrode.

It is now disclosed for the first time a method for treating biological tissue using a shaped plasma profile. The presently disclosed method includes: (a) providing a gas flow, (b) igniting gas from the gas flow to produce a plasma gas-discharge, (c) subjecting a surface of the biological tissue to the plasma gas-discharge, and (d) using electromagnetic interactions between the subjected surface of the biological tissue and the plasma gas-discharge traversing an electromagnetic interaction gap, shaping a profile of the plasma gas-discharge, thereby treating the biological tissue.

It is now disclosed for the first time a method for transdermal ion delivery of a plasma flux to biological tissue as a means of treating the biological tissue. The presently disclosed method includes: (a) subjecting a surface of the biological tissue to a plasma flux of a plasma gas discharge, and (b) transdermally delivering the plasma flux to the biological tissue beneath the surface.

According to some embodiments, the step of transdermally delivering the plasma flux further includes transdermally delivering a plasma flux of at least one species selected from the group consisting of: atomic ions, molecular ions, atomic radicals, molecular radicals, excited-state ions, excited-state radicals, energetic ions, energetic radicals, cooled ions, cooled radicals, energetic electrons, and any components of feed gas.

These and further embodiments will be apparent from the detailed description and examples that follow.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice.

In the drawings:

FIG. 2 is a simplified schematic diagram illustrating a regular nozzle-electrode configuration which yields a laminar gas flow characteristic, and its associated torch-type plasma profile according to some embodiments of the exemplary system.

FIG. 3 is a simplified schematic diagram illustrating a regular nozzle-electrode with a dielectric cylindrical cavity attachment which yields a plasma that substantially fills the total cavity volume, and its associated plasma profile according to some embodiments of the exemplary system.

DETAILED DESCRIPTION OF THE INVENTION

Figure 1A:
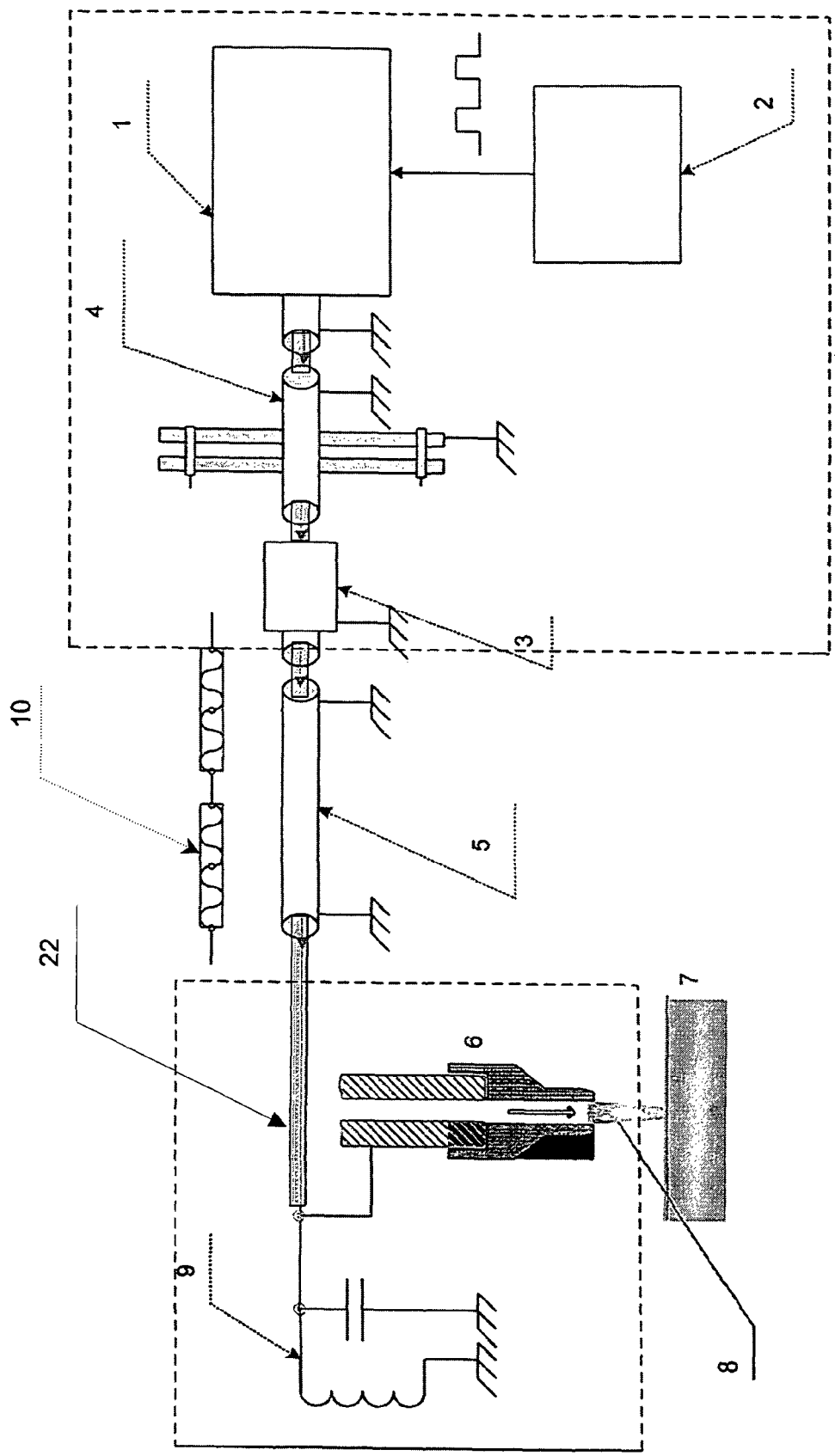
FIG. 1A is a simplified schematic diagram illustrating various components of the RF plasma gas-discharge device, and their interconnectedness, according to some embodiments of the exemplary system.

Embodiments of the exemplary system provide a device and a method for treating biological tissue using a shaped plasma profile.

The principles and operation of device for treating biological tissue using a shaped plasma profile according to some embodiments of the exemplary system may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. In addition, it is to be understood that the phraseology and terminology employed herein is for the purpose of description and should not be regarded as limiting.

FIG. 1A provides a diagram of a device for treating biological tissue using a shaped plasma profile according to exemplary embodiments of the exemplary system. The device includes an RF power generator (amplifier) 1 capable of producing an output RF power 10 directed to an electrode, a nozzle-electrode 6, contactable with a surface of biological tissue 7. Nozzle-electrode 6 is capable of delivering a desired amount of energy to gas flow 9 at or above atmospheric pressure. Nozzle-electrode 6 is configured within the device to facilitate the formation of a current path to the surface of biological tissue and ignite the gas flow 9 into a plasma discharge upon encountering the biological tissue by the nozzle-electrode 6.

As used herein, when a electrode or nozzle electrode is said to be configured "within the device" to provide a specific functionality, this relates to at least one of (a) the intrinsic physical or geometric properties of the electrode (b) the geometric configuration of the electrode relative to other device elements (such as device housing); and (c) the functional relation of the electrode relative to other device elements, (for example one or more electrical components of the device). It is noted that the term "within the device" is not meant to imply that the electrode is required to be physically within one or more device elements, such as device housing. In fact, in some embodiments, the electrode configured within the device is disposed relative to device housing so as to be outside of the housing.

The exemplary system described herein further includes a pulse-width modulation (PWM) controller 2 which regulates output RF power 10 coming from RF power generator 1 to have a predetermined duration and amplitude with a desired frequency using rectangular pulses. For example, at an operating RF frequency of 40.68 MHz, PWM-frequency is 50 Hz to 20 kHz and with a duty cycle of 2 to 100%. This control is important in the case of obtaining an atmospheric plasma gas-discharge 8 by providing the desired level of average RF power that goes into plasma gas-discharge 8. It further enables high amplitude RF power (an instantaneous power pulse) that is critical for igniting plasma gas-discharge 8. Furthermore, since it is known that the voltage of plasma gas-discharge 8 is constant (or slightly increasing) with increasing power input, increasing RF power will increase plasma gas-discharge current by increasing plasma gas-discharge volume in normal discharge mode or current density in abnormal discharge mode. By plasma gas-discharge, we mean a plasma, and optionally, a gas-discharge.

PWM controller 2 provides a modulated RF power with a frequency much lower than basic RF power (e.g. 40.68 MHz is basic sinusoidal oscillations and 10 kHz rectangular modulation). PWM controller 2 is an important component in our system because it provides a high level of RF voltage acting in the gas-discharge volume with a desired level of average RF power. A high level of RF voltage (or amplitude of RF power) is necessary for sustaining plasma gas-discharge 8. and application of simple fixed IMNs. In this case IMN does not see a time dependence of RF power and acts with the same RF power amplitude. The average level of the RF power could be low in operation.

The exemplary system further includes a phase shifter (e.g. trombone-type phase shifter 4) connected to RF power generator 1. Phase shifter 4 is capable of shifting a phase of directed traveling waves of output RF power 10 so that energy therefrom is concentrated primarily into plasma gas-discharge 8, which facilitates an ignition stage and an operation stage of plasma gas-discharge 8.

The exemplary system further includes an impedance-matching network (IMN) 3 connected to phase shifter 4 and nozzle-electrode 6 capable of capable of converting an aggregate impedance of the device including plasma gas-discharge 8, nozzle-electrode 6, and biological tissue 7 (DNT—discharge-nozzle-tissue) from a nominal value (e.g. 250-350 Ohms) to a corrected value (e.g. 50 Ohms). The corrected value matches a characteristic impedance of RF power generator 1 and phase shifter 4 so that the output traveling wave may sustain plasma gas-discharge 8 without being converted to a standing wave.

A high level of RF voltage (or amplitude of RF power) is necessary for using IMN 3 on a fixed mode. In this case, IMN 3 does not see a time-dependence of RF power, and therefore responds with the same RF power amplitude. Thus, it should be taken into account that the average amplitude of RF power acting in the plasma gas-discharge v olume can be lower than the RF power amplitude. IMN 3 can be a fixed or variable IMN of various types (e.g. L, T, π-types or more complicated units).

The exemplary system further includes an RF resonator 5 connected to IMN 3 and to nozzle-electrode 6 capable of cyclically accumulating and releasing a desired amount of energy for an operation stage. RF resonator 5 is further capable of concentrating a desired amount of energy for an ignition stage. This is critical to enabling different gas compositions to be used in plasma gas-discharge 8. A change in gas composition will change the ionization potential of the gas. RF resonator 5 has a high Q-factor (i.e. greater than 100). RF resonator 5 is preferably a parallel-type consisting of an inductor and capacitor connected in parallel. The interconnections between RF power generator 1, PMW controller 2, IMN 3, phase shifter 4, RF resonator 5, and nozzle-electrode 6 are made with a feeding transmission cable 22. Characteristics of feeding transmission cable 22 will be described later.

The exemplary system further includes nozzle-electrode 6 capable of conveying output RF power 10 from RF power generator 1 (with appropriate energy control from PMW-controller 2) into gas flow 9 to ignite and stabilize plasma gas-discharge 8 which is used to treat biological tissue 7 after output RF power 10 has been processed by phase shifter 4, IMN 3, and resonator 5.

Typically, operation of the device results in 2-4% loss of energy from output RF power 10 with an additional 2-4% reflection of energy from output RF power 10. This means that the device can reliably deliver 90-95% of energy from output RF power 10 into plasma gas-discharge 8. Neither, concentration of energy from output RF power 10, nor this degree of efficiency, was achievable with previously available alternatives. IMN 3 reduces reflection of output RF power 10 from surface of biological tissue 7, thereby increasing efficiency of delivery of energy to plasma gas-discharge 8.

Figure 1B:
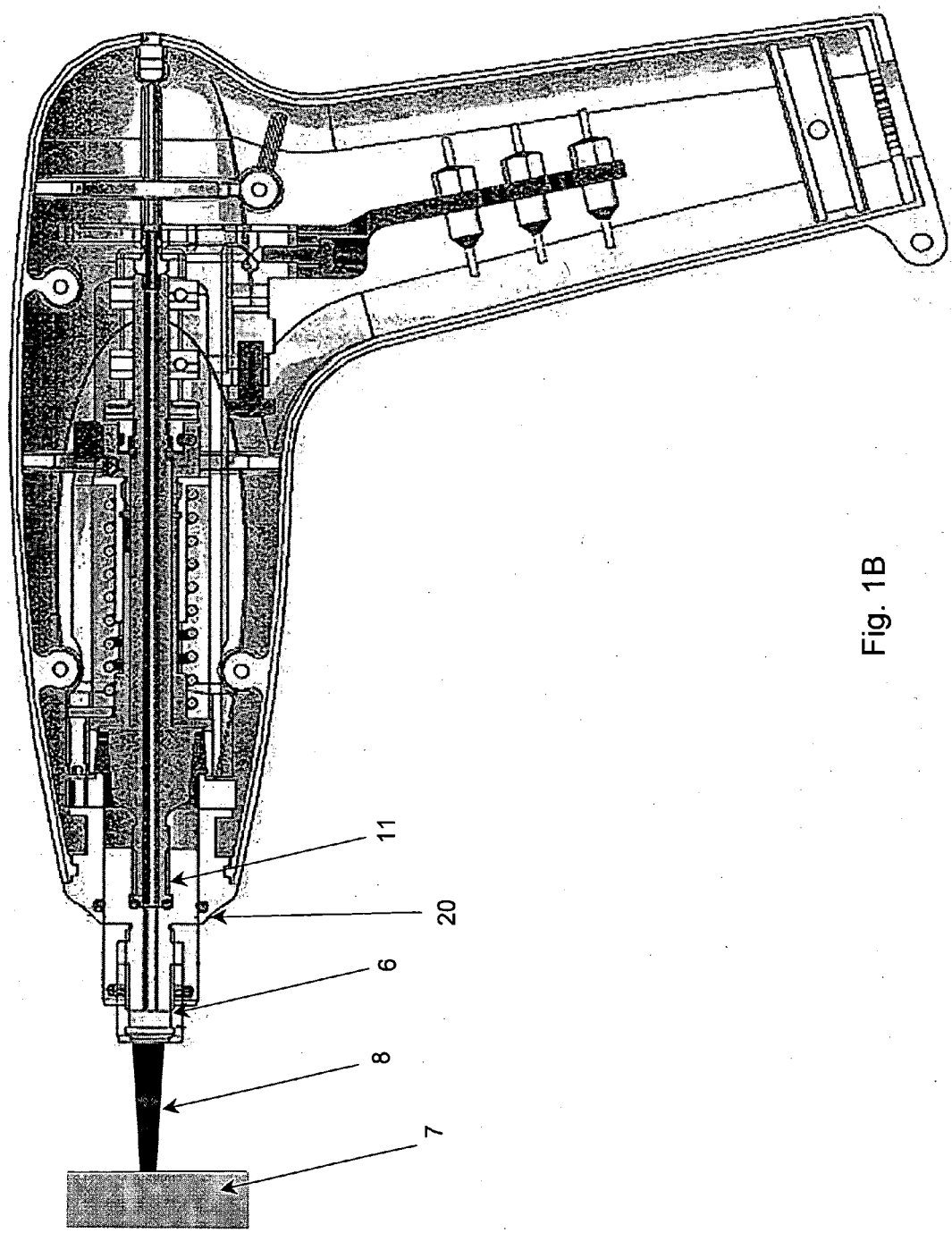
FIG. 1B is a simplified schematic diagram illustrating the physical relationship of the nozzle-electrode to the device housing according to some embodiments of the exemplary system.

In FIG. 1B, a cross-section of the device in the region where plasma gas-discharge 8 is obtained is schematically illustrated. FIG. 1B serves to highlight one of the inherent advantages of the exemplary system over the prior art. The elements of important detail are the relative positions of nozzle-electrode 6, housing 20, and plasma gas-discharge 8. Nozzle-electrode 6 is engaged to housing 20 using an electrode holder 11. It should be made clear that housing 20 is not an electrode in and of itself. As illustrated in exemplary embodiments of FIG. 1B, electrode holder 11 is a dual purpose component that also serves as a gas inlet for receiving the gas flow from a gas source (not shown), though it is appreciated this is not a limitation of the exemplary system, and that in some embodiments the gas inlet is provided separately. Furthermore, it is noted that although the "gas inlet" as illustrated in FIG. 1B receives gas from a location outside of the housing of the device, this is not a limitation of the exemplary system.

In the configuration illustrated in FIG. 1B, nozzle-electrode 6 is substantially electrically unshielded by housing 20, thereby enabling nozzle-electrode 6 to electromagnetically interact with surface of biological tissue 7. For clarification, it should be noted that the inlet of nozzle-electrode 6 receives gas from electrode holder 11, and that plasma gas-discharge 8 is formed outside nozzle-electrode 6 (i.e. at its outlet).

Further, the absence of a ground electrode from the device permits the plasma gas discharge 8 to be shaped which enables various types of skin treatments. As used herein, "shaping" of plasma gas discharge includes both changing or altering a shape of a profile as well as maintaining shape of the profile.

Figure 1C:
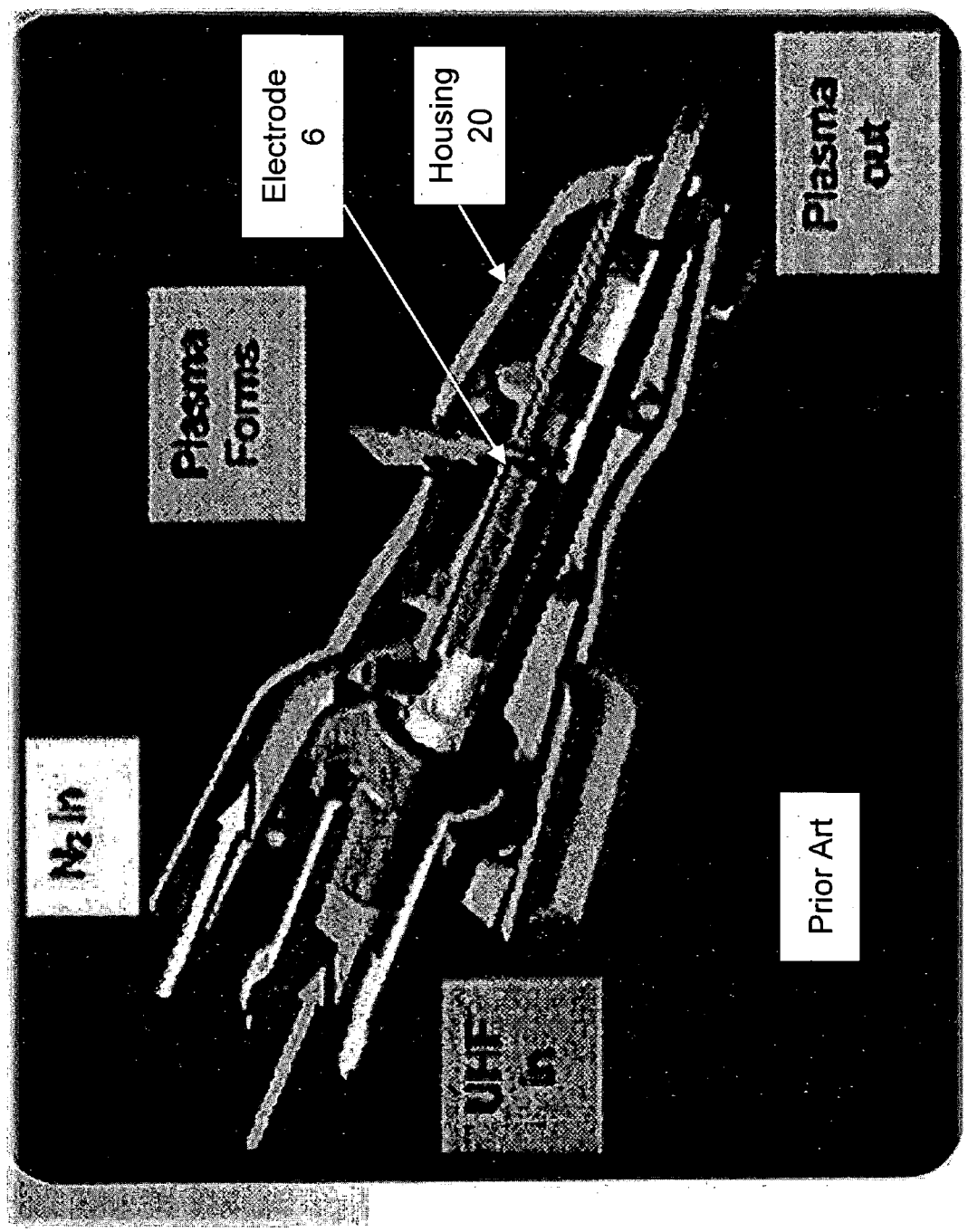
FIG. 1C is a simplified schematic diagram illustrating physical relationship of the electrode to the device housing according to the prior art device of Gyrus.

In sharp contrast, FIG. 1C schematically illustrates the teaching of the prior art of Gyrus which clearly shows electrode 6 positioned completely within housing 20. This configuration prevents electromagnetic interaction of electrode 6 with any surface exterior to housing 20 which electrically shields the device. In doing so, this limits the achievable shape of the plasma gas-discharge profile to only one form, namely a torch-type tip. This also limits the control over parameters such as current density and discharge cross-section.

In contrast, embodiments of the exemplary system provide for a plasma profile which can be shaped in a versatile "configurable" manner, using an electrode (e.g. a nozzle-electrode) that is reversibly deployable to the device housing. Thus, one can conveniently select the desired plasma gas profile by selecting the electrode (e.g. nozzle-electrode) appropriate for the targeted desired plasma gas profile, and engaging the selected electrode to the device housing.

Before describing the various configurations of nozzle-electrodes, a general description of how the shape and dimension of a nozzle-electrode affects the characteristics of a plasma gas-discharge will be presented.

A plasma gas-discharge can be produced in two modes: a diffusive type and a constricted type. Both types of plasma gas-discharges are suitable for treatment of biological tissue. The diffusive-type plasma gas-discharge does not provide a high power density. This mode is characterized by high voltage and low current. The concentration of charged particles is low (e.g from $10^{-2}$ to $10^{-3}$, i.e. the ratio of ions to neutrals, or 0.1-1%). The discharge is highly uniform (or homogeneous). This mode is applicable to heating and bio-photostimulation of biological tissue.

Constricted-type plasma gas-discharges are inhomogeneous, and have hot zones with high concentrations of ions and electrons. The neutral temperature of the plasma gas-discharge is also high, while the discharge volume is low. This mode is applicable for biological tissue ablation, evaporation, and cutting.

The shape and dimension of a nozzle-electrode is important. When directly contacting the biological tissue, the nozzle-electrode provides a pure plasma gas-discharge environment where the gas fills the entire volume of the nozzle-electrode, decreasing interaction of ambient air into the treatment region. The plasma profile will depend on the shape of the nozzle-electrode. For a diffusive-type plasma gas-discharge, the process can be characterized as an abnormal RF glow-discharge. This means that the plasma gas-discharge increases in current density as RF power increases. This plasma gas-discharge process (i.e. abnormal) is more energetic than a normal plasma gas-discharge process.

When the nozzle-electrode is not in contact with the biological tissue, the gas flow is actively mixed with ambient air. The concentration of pure gas will decrease as the distance of the biological tissue from the nozzle-electrode increases. The mixing will be most active at the periphery of the gas stream due to turbulent currency there. Therefore, plasma profile will be similar to a plasmatron, or tongue-type. In this normal plasma gas-discharge process, the plasma gas-discharge volume increases as the RF power increases. The plasma gas-discharge density in this case is not high.

FIG. 2 schematically illustrates a regular nozzle-electrode 6 attached to electrode holder 11. Gas flow 9 enters the nozzle-electrode which is energized to produce plasma gas-discharge 8 which interacts at a distance of 3-5 outlet diameters with surface of biological tissue 7. In this configuration, a plasma profile having a torch-type tip is produced. Gas flow 9, in this case, has laminar characteristics. The plasma gas-discharge is ignited between the outlet of nozzle-electrode 6 and surface of biological tissue 7.

FIG. 3 differs from FIG. 2 in that plasma-gas discharge 8 is not open to the surrounding atmosphere (as it is in FIG. 2). In this configuration, a dielectric cylindrical cavity attachment 12 isolates plasma gas-discharge 8 from surrounding atmosphere. Whereas, in FIG. 2, plasma gas-discharge 8 was allowed to interact with air to form the torch-type tip, the configuration of FIG. 3 provides plasma gas-discharge 8 substantially occupying the total cavity volume.

Figure 4:
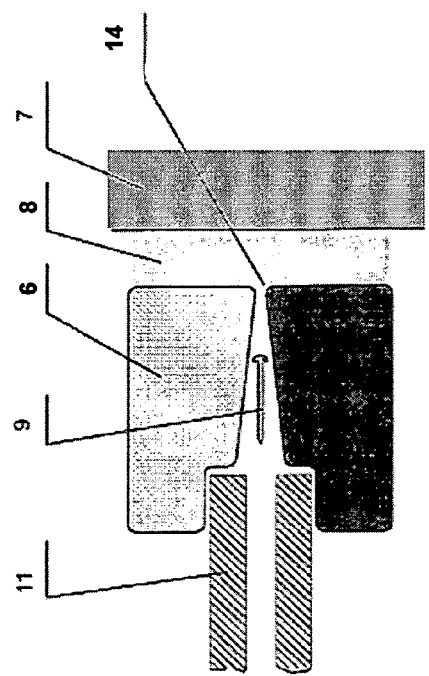
FIG. 4 is a simplified schematic diagram illustrating a nozzle-electrode configuration which yields low current density and high discharge cross-section due to a turbulent gas flow characteristic, and its associated plasma profile according to some embodiments of the exemplary system.

Another configuration is schematically illustrated in FIG. 4. Nozzle-electrode 6 is dimensioned to have the inlet diameter much larger (i.e. 10-20×) than outlet diameter 14. Furthermore, it has an external diameter much greater (i.e. 3-6×) than the gap between nozzle-electrode 6 and surface of biological tissue 7. This leads to gas flow 9 having a turbulent characteristic. The combination of gas flow 9 with nozzle-electrode 6 in this configuration results in plasma gas-discharge 8 occupying the entire volume between nozzle-electrode 6 and surface of biological tissue 7. Features of this configuration are very low current density (e.g. peak current density is 100-700 mA/cm$^2$ and average values are 10-200 mA/cm$^2$) and high discharge cross-section (e.g. 2-4 cm$^3$). This configuration is most suitable for treating large surfaces that do not require high current density.

Figure 5:
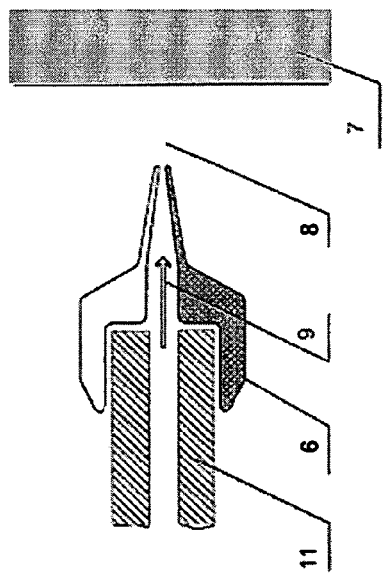
FIG. 5 is a simplified schematic diagram illustrating a nozzle-electrode configuration which yields a very high current density and very low discharge cross-section, and its associated plasmatron plasma profile with a narrow flame-tongue tip according to some embodiments of the exemplary system.

The opposite case (to that in FIG. 4) is schematically illustrated in FIG. 5. Nozzle-electrode 6 is very small, the pressure drop is high and gas flow 9 is high. The area of interaction of nozzle-electrode 6 and surface of biological tissue 7 is very small. Thus, plasma gas-discharge 8 is formed as a narrow flame-tongue (plasmatron-type) tip. The current density in this case is extremely high (i.e. 10-20 times greater than the previous configuration). This configuration is most suitable for ablating and cutting biological tissue.

It is also possible in this configuration to obtain a supersonic jet of plasma gas-discharge 8 through adiabatic expansion of gas flow 9 as it exits nozzle-electrode 6. In doing so, this configuration enables treatment of surface of biological tissue 7 via transdermal ion delivery.

To clarify, by surface of biological tissue, we mean the outer surface and near-surface region which includes underlying layers of tissue such as dermis and subcutaneous layers.

Figure 6:
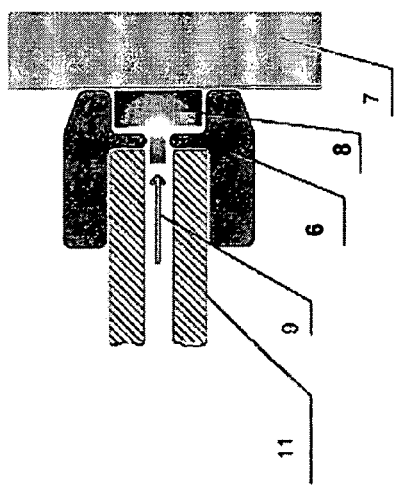
FIG. 6 is a simplified schematic diagram illustrating a bowl nozzle-electrode configuration which enables simultaneous RF heating and plasma operation due to the biological tissue being a non-equipotential surface and yields a plasma that substantially fills the total internal volume, and its associated plasma profile according to some embodiments of the exemplary system.
Figure 7:
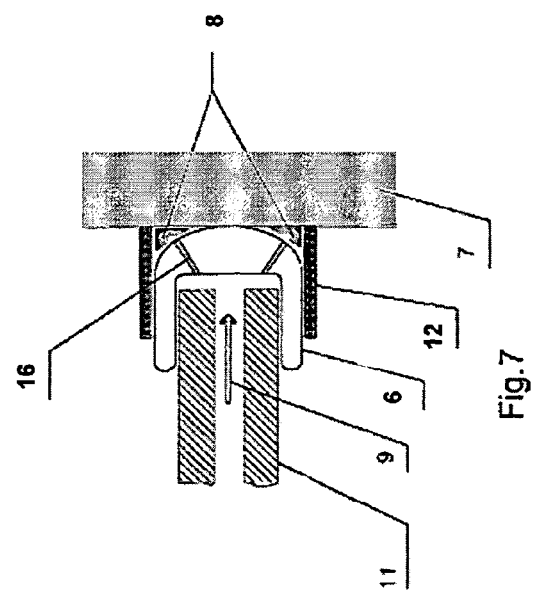
FIG. 7 is a simplified schematic diagram illustrating a spherical nozzle-electrode configuration with a dielectric cylindrical cavity attachment which enables simultaneous RF heating and plasma operation due to the biological tissue being a non-equipotential surface and yields a plasma that substantially fills the total internal volume, and its associated ring-type plasma profile according to some embodiments of the exemplary system.

FIGS. 6 and 7 schematically illustrate processes that combine RF-heating and plasma gas-discharge treatment. In both of these configurations, surface of biological tissue 7 is a non-equipotential surface. Therefore, a single electrode, nozzle-electrode 6, can simultaneously heat surface of biological tissue 7 and maintain plasma gas-discharge 8.

FIG. 6 schematically illustrates the first implementation of this configuration wherein nozzle-electrode 6 is designed as a bowl. The outer edge of this bowl is in the direct contact with surface of biological tissue 7 while gas flow 9 is supplied into internal area of the bowl. Plasma gas-discharge 8 exists in this internal area.

FIG. 7 schematically illustrates the second implementation of the described configuration wherein nozzle-electrode 6 has a spherical surface and is partially contacting surface of biological tissue 7 directly. Plasma gas-discharge 8 is produced through several small peripheral holes 16 in spherical nozzle-electrode 6. The dielectric cylindrical cavity attachment 12 provides a sustainable ring-type plasma gas-discharge 8.

Figure 8:
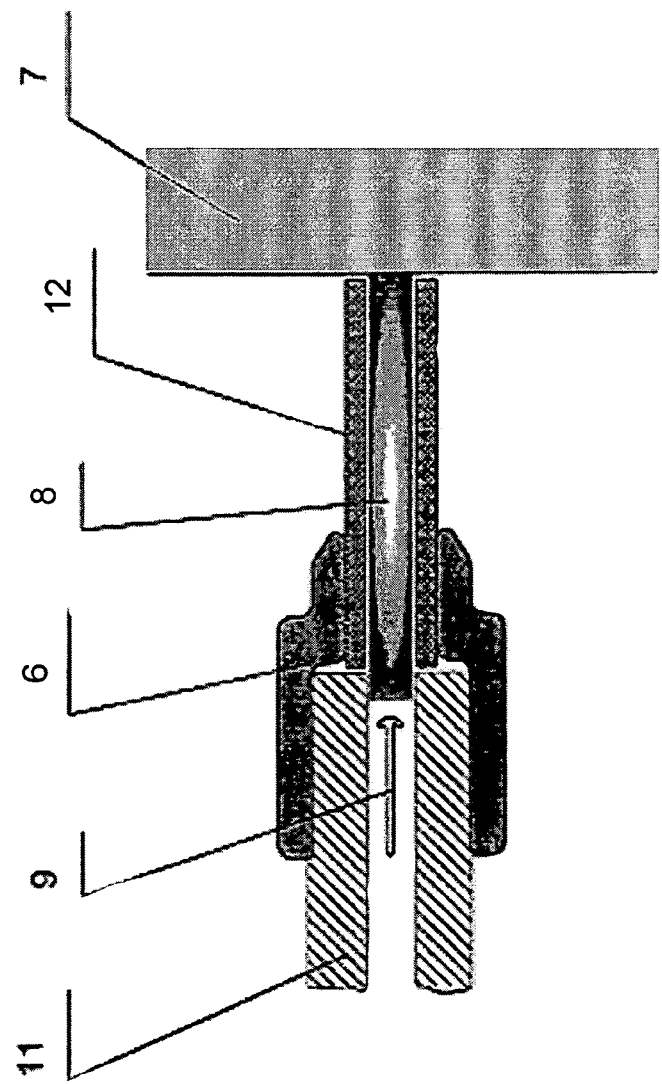
FIG. 8 is a simplified schematic diagram illustrating a regular nozzle-electrode configuration with a dielectric cylindrical conduit attachment extending into the interior of the nozzle-electrode which yields a plasma gas-discharge ignited in the conduit and is transported to the tissue via a flow of gas, and its associated plasma profile according to some embodiments of the exemplary system.

The configuration schematically illustrated in FIG. 8 involves plasma gas-discharge 8 being ignited within dielectric cylindrical conduit attachment 12 which extends into interior of nozzle-electrode 6. Dielectric cylindrical conduit attachment 12 is preferably made of quartz or glass. The end of dielectric cylindrical conduit attachment 12 is in contact with surface of biological tissue 7. Plasma gas-discharge 8 is transported to surface of biological tissue 7 by gas flow 9. The nozzle-electrode 6 ignites plasma gas-discharge 8.

The exemplary system further embodies a method which includes two stages: a plasma gas-discharge ignition stage and an operation stage.

The ignition stage is a time-limited transition stage that could take from several milliseconds to several microseconds (the higher operating gas static pressure shortens the duration of the ignition stage). For ignition, it is necessary to reach a certain threshold voltage (integral parameter) in the discharge region, or an RF field strength (differential parameter) in a localized area of the discharge region. The discharge breakdown starts from this area and spreads out through the areas where the RF potential (or field strength) is enough for the discharge to be sustained.

Many factors facilitate the ignition stage such as: decreasing gas pressure (up to lower point of Paschen curve), shape of nozzle-electrode 6, dimensions of nozzle-electrode 6, distance between nozzle-electrode 6 and surface of biological tissue 7, kind of gas or gas combination, and uniformity of electrical potential distribution.

In order to produce a plasma (ionized gas) in a desired volume, it is necessary to supply an electromagnetic field strength higher than that of the threshold field. Thus, the process of ignition of a plasma gas-discharge is a breakdown of the gas medium. The threshold field strength depends on a variety of factors (e.g. gas pressure, gas composition, presence of contamination, electromagnetic field/wave parameters, electrode shape, and electrode material). It is also understood and noted that there are certain types of discharges that do not need electrodes (e.g. optical discharge, etc.).

The difference between a plasma and plasma gas-discharge 8 is that a plasma needs to meet a condition of quasi-neutrality. That means that the number of positively charged particles should be equal to the number of negatively charged particles. Plasma gas-discharge 8 actually has zones that contain a plasma and zones that do not.

During the ignition stage (before plasma gas-discharge stabilization), a certain problem exists. It is evident that at this stage of the process, the impedance of the system without plasma gas-discharge 8 is very different than the impedance of the system with plasma gas-discharge 8. Therefore, the optimal impedance of IMN 3 for the ignition stage may not be optimal after ignition (during the operation stage). The main tasks of IMN 3 during the ignition stage are to minimize the reflected RF power to RF power generator 1, and to provide a necessary RF field strength in the area of gas breakdown. Reflected power before a plasma gas-discharge ignition is very high (i.e. 80-90% of incident power). The active losses and impedance of the system depends on the length of cable between RF power generator 1 and IMN 3.

Therefore, the ignition stage also depends on the phase shift of the electromagnetic wave (provided by phase shifter 4), and the amplitude of the electromagnetic wave propagating between nozzle-electrode 6 and surface of biological tissue 7. By adjustment of phase shifter 4, it is possible to produce a minimum, as well as a maximum, of the electromagnetic wave at the targeted region of surface of biological tissue 7. When plasma gas-discharge 8 is ignited, the phase shift becomes less important because a traveling wave is established and the necessary amplitude of RF voltage is substantially lower than during the ignition stage.

There are several ways to control both the ignition and operation stages. Different configurations of IMN 3 can be used for the ignition and operation stages. This can include switching between fixed IMN mode and variable IMN mode (using variable capacitors or inductors). Thus, to use the same IMN that provides both functionalities, a specially-configured IMN is necessary for IMN 3. Similary, feeding transmission cable 22 between IMN 3 and an RF power generator 1 has to be appropriately chosen in order to supply both functions. Furthermore, the same can be stated for phase shifter 4. To use the same phase shifter that can provide a necessary phase jump from a state 1, optimal for the ignition stage, to a state 2, optimal for the operation stage, a specially-configured phase shifter is necessary for phase shifter 4.

In order to treat surface of biological tissue 7 with plasma gas-discharge 8, there are several possibilities of arranging the electrodes. In the case of the prior of Gyrus cited above, the discharge (high-frequency type) is produced in the region between two electrodes, and then transported to the area of treatment. The gas flow is the main transporting agent of charged particles generated in the discharge area. This system is similar to a plasmatron design. The system contains two or more electrodes which render it self-sufficient, meaning it does not need biological tissue for its operation. In principle, the target of the discharge is not important. It could be plastic, biological tissue, a metallic surface, or some other surface.

In the exemplary system, the case is opposite. Surface of biological tissue 7 serves as a second (or virtual) electrode (e.g. ground electrode), and the external surface of nozzle-electrode 6 serves as a "hot" electrode. When surface of biological tissue 7 is located in proximity to nozzle-electrode 6, surface of biological tissue 7 and nozzle-electrode 6 form an electrodynamic structure characterized by a specific aggregrate impedance. Therefore, surface of biological tissue 7 serves as a ground electrode for charged particles, closing a path of RF current, and influences the aggregate impedance of the system during the discharge breakdown process, distribution, and steady-state. Thus, the entire device shown in FIG. 1 can be symbolically described as an electrical circuit, where the critical role of surface of biological tissue 7 is to close the circuit. We use the word "proximity" to mean within a short distance (i.e. <50 cm.). We use "upon encountering" to mean "being brought into proximity" which will be used later in this application.

As described above, an aggregate impedance of the DNT system is matched to the characteristic impedance of feeding transmission cable 22 (e.g. 50 Ohms). Therefore, the best conditions of electromagnetic traveling wave propagation (i.e. no reflection power) are achieved only with the presence of the tissue.

Figure 9:
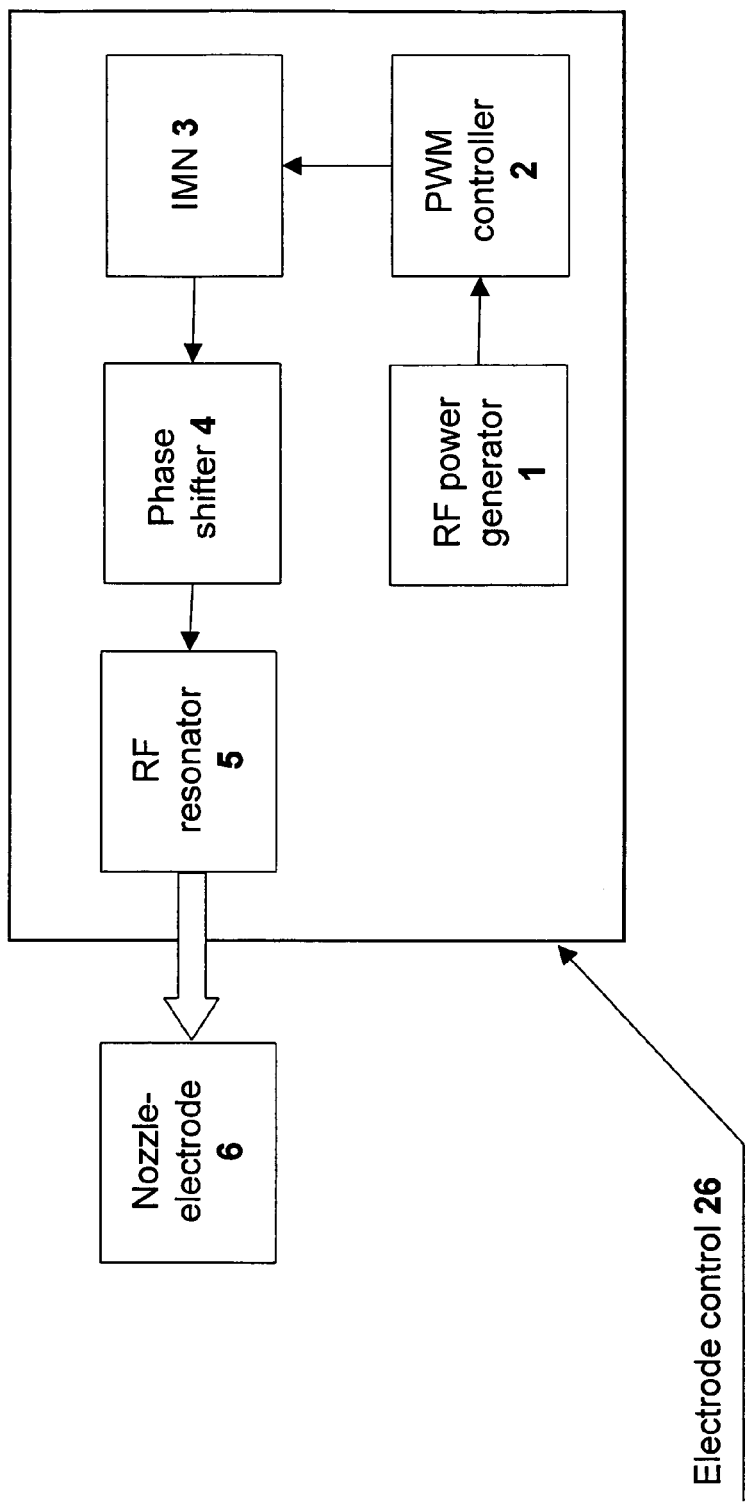
FIG. 9 is a simplified schematic diagram illustrating various components of the electrode control and their interconnectedness, according to some embodiments of the exemplary system.

The device components of RF power generator 1, PWM controller 2, IMN 3, phase shifter 4, and RF resonator 5 can be thought of as a conglomerate device to provide a suitable power characteristic to nozzle-electrode 6, enabling a path of current from plasma gas-discharge 8 to surface of the biological tissue 7 to form. FIG. 9 is a simplified schematic diagram illustrating various components of an electrode control 26 and their interconnectedness, according to some embodiments of the exemplary system. This is one embodiment of what will be referred to later in this application as an "electrode control". It is appreciated that other embodiments of electrode control 26 are possible with different configurations, additional, and or fewer device components.

The operation stage is characterized by a voltage that is appreciably lower than the ignition stage potential (voltage). In our case, a critical role of the biological tissue in the progression of the discharge from ignition stage to operation stage is the following. The biological tissue distorts an RF field (or electromagnetic wave propagation) creating stronger fields in the interaction gap between nozzle-electrode 6 and surface of biological tissue 7, thereby facilitating, or in the most cases triggering, a discharge ignition.

The operation stage is a stable, time-independent process, and requires an RF voltage that is lower than the voltage necessary for the ignition stage. IMN 3 operates during both the ignition and operation stages of plasma gas-discharge 8. In order to match the impedance of plasma gas-discharge 8 with RF power generator 1, it is necessary for IMN 3 to convert the aggregate impedance of the DNT system into an operating output impedance of RF power generator 1 (typically 50 Ohms). During the operation stage, precise matching of impedances results in practically no reflected RF power, meaning an SWR (standing wave ratio) close to one (i.e. practically no standing wave). This yields a pure traveling wave that is totally absorbed by a resistive load (i.e. plasma gas-discharge 8 and surface of biological tissue 7).

Surface of biological tissue 7 serves not only as an electrode, but also as a dissipator of part of the RF power. The impedance of biological tissue is approximately 300 Ohms with weak negative reactance. It can be simulated by a 300 Ohm resistor with a 1.5-2.5 pF capacitor placed in parallel to it. Thus, plasma gas-discharge 8 and surface of biological tissue 7 act as a resistive load for RF power generator 1.

The dissipation of RF power is 85-95% in plasma gas-discharge 8, and 5-15% surface of biological tissue 7 because the maximum of electromagnetic field density is closest to nozzle-electrode 6. Since surface of biological tissue 7 is located several centimeters from nozzle-electrode 6, the real dimension of surface of biological tissue 7 interacting with the RF field is large (i.e. 20-40 cm$^2$). Thus, the "virtual" resistance of surface of biological tissue 7 in this case is much lower than the resistance in the case of direct contact of surface of biological tissue 7 and nozzle-electrode 6.

The electrodynamic model for this system is two resistors placed in series with a reactance element, such as a capacitor, placed in parallel. The total resistance depends on the type of nozzle-electrode 6, and distance between surface of biological tissue 7 and nozzle-electrode 6. For example, in the case of the first implementation of nozzle-electrode 6 shown in FIG. 2 at a distance 1 cm. surface of biological tissue 7, the total resistance of the configuration (plasma gas-discharge 8 and surface of biological tissue 7) is 400 Ohms, where resistance of plasma gas-discharge 8 is 350 Ohms and resistance of surface of biological tissue 7 is 50 Ohms. Therefore, if the RMS RF-power amplitude of plasma gas-discharge 8 is 350 Watts, then the power dissipation is 50 watts in surface of biological tissue 7 and 300 Watts in plasma gas-discharge 8.

The dissipated RF power in plasma gas-discharge 8 is converted into kinetic and potential energy of the plasma gas-discharge particles which represents the bulk of the energy because RF emission is dissipated in biological tissue.

This interaction gap is not to be confused with the physical gap between the outermost edge of the device and surface of biological tissue 7 which may or may not be the same. In the case of the prior art of Gyrus in FIG. 1C, the interaction gap does not extend beyond housing 20; and therefore does not involve any biological tissue. Whereas, the physical gap of the prior art is obviously the gap between housing 20 and their target surface.

Once the ignition is sustained in the operation stage, the discharge can be maintained as long as is necessary for the desired treatment.

While the preferred embodiment involves a diffusive plasma gas-discharge, other types of discharges are possible. The preferred embodiment results in low electron temperature and concentration which is favorable to treatment of biological tissue. This type of discharge is spread over the desired region of the biological tissue. Parameters of this type of discharge are controllable such as: power, current density and geometry, and particularly position.

The active species (plasma flux) of the plasma gas-discharge in all configurations include at least one of the species selected from the group consisting of: atomic ions, molecular ions, atomic radicals, molecular radicals, excited-state ions, excited-state radicals, energetic ions, energetic radicals, cooled ions, cooled radicals, energetic electrons, and any components of the gas. The ability to electrically bias the nozzle-electrode 6 relative to surface of biological tissue 7 facilitates an ionic gas flow to surface of biological tissue 7.

As was described previously, there are two types of plasma gas-discharges: constricted type and diffusive type. Diffusive-type plasma gas-discharges are mostly used for therapeutic applications such as heating, bio-photostimulation, or ionic shower (i.e. treatment by chemically- and biologically-active particles (ions, free radicals etc.). Constricted-type plasma gas-discharges can cut, ablate, and/or evaporate a biological tissue because there is a high density of energy (i.e. low plasma gas-discharge volume). The active components of the system on the biological tissue can be: the RF field, electrons, positive ions, negative ions, free radicals, light emission (photons), neutrals, and the gas stream (or flow).

In a diffusive-type plasma gas-discharge, an estimate of RF power directly dissipated into biological tissue is 5-10% of the total RF power input. The RF power dissipating in the biological tissue increases the temperature of the tissue by inducing RF currents and rotationally exciting dipole molecules (mostly water molecules).

The concentration of free electrons is approximately equal to the concentration of positive ions. Negative ion concentration depends on gas composition, and is typically very low; it is negligible for inert gases. The concentration of free electrons is $10^{-2}$-$10^{-3}$ (i.e. 0.1-1%). Given a very low electron mass and a high average kinetic energy (3-8 eV), electron excitation of particles in biological tissue is possible. The majority of electron energy is consumed by the plasma gas-discharge itself. This is primarily channeled into neutral particle excitation (both atomic and molecular electronic and rotational levels).

The concentration of positive ions is low with a low energy. The temperature of positive and negative ions is equal to the temperature of neutral particles, and is close to room temperature. Therefore, the kinetic energy of ions, as well as neutral particles, is not a major channel for conveying the plasma gas-discharge energy to biological tissue. Furthermore, the gas flow does not add substantial energy as well.

The RF field imparts electromagnetic energy mostly to the electron channel. The electron energy distribution function maximum of diffusive-type plasma gas-discharges is 3-8 eV region. Ionization of the plasma gas-discharge accounts for 10-15% of electron energy, the remainder goes into the various excitation channels mentioned above. Therefore, the most efficient process in diffusive-type plasma gas-discharges is an excitation of neutral particles. The lifetime of the particle in the excited state depend on many factors such as gas pressure, gas composition, and gas type. The excited particles can be metastable states with lifetimes up to one second. The excited particles lose potential energy through internal collisions, photon radiation, and interaction with the biological tissue. Due to the presence of the gas flow, the most significant process will be an interaction of excited particles with biological tissue.

The biological tissue is also irradiated with emitted light. It is known from the literature that bio-photostimulation can be achieved (e.g. stimulation of mitochondria cells with radiation of He—Ne laser at 6328 Angstrom wavelength). If the plasma gas-discharge is produced using a gas mixture similar to that used in a He—Ne laser, the energy from excited (metastable state) neutral Ne atoms can be efficiently imparted to biological tissue via inelastic collisions. The efficiency of this process is much greater than in the case of a He—Ne laser. In the case of the laser, the excited Ne atoms irradiate biological tissue with photons after deexcitation. Therefore, the efficiency is very low (<1%). In the case of plasma gas-discharges, the excited particles interact with biological tissue directly.

Free radicals and chemically-active molecules can also undergo chemical reactions with biological tissue. The treatment of biological tissue with excited $CO_2$ from a plasma gas-discharge is an example of an important process.

While nozzle-electrode 6 is conducting (e.g. Au, Ag, Cu, Al), the method of the preferred embodiment utilizes an aluminum nozzle-electrode with an exterior alumina coating. This results in a diffusive discharge without electron emission from nozzle-electrode 6.

Furthermore, the method of operation for various treatments would not only determine the choice of nozzle-electrode 6 and parameters of gas flow 9, but also the choice of gas. For example, for an ablation treatment, one preferred embodiment of the method would utilize approximately 5% $O_2$ and 95% Helium. This is primarily due to the role of oxygen as an oxidant.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the exemplary system.

What is claimed is:

1. A device for treating biological tissue, the device comprising:
   (a) a device electrode;
   (b) an RF power generator configured to produce RF power directed to the device electrode so as to ignite a gas flow, thereby generating a diffusive plasma gas discharge within the gas flow in an interaction gap between the device electrode and the biological tissue, the diffusive plasma gas discharge having a ratio of ions to neutrals within the generated plasma gas-discharge that is less than 0.01;
   (c) an impedance matching network configured to reduce reflection of the RF power produced by the RF power generator from a surface of the biological tissue to the RF power generator;
   (d) a transmission line;
   (e) a resonator; and
   (f) device housing for providing support for the device electrode, wherein:
      (i) the device operates at or above atmospheric pressure;
      (ii) the device electrode is substantially electrically unshielded by the device housing;
      (iii) the impedance matching network, the resonator and the transmission line electrically connect the device electrode to the RF power generator;
      (iv) the impedance matching network, the resonator and the transmission line are configured to operate so that, prior to the ignition of the gas flow, distortions by the biological tissue of the RF field of the RF power generated by the RF power generator create a stronger field within the interaction gap, thereby triggering the ignition of the gas flow to produce the diffusive plasma gas discharge; and
      (v) the RF power generator is configured to operate, after the ignition of the gas flow, by way of the impedance matching network, the resonator and the transmission line to sustain the gas plasma discharge.

2. The device of claim 1 wherein the device electrode is configured so that the diffusive plasma gas-discharge is shaped by the electromagnetic interaction between the device electrode and the surface of the biological tissue.

3. The device of claim 1 wherein the device electrode is a nozzle-electrode including a nozzle portion adapted to receive the gas flow.

4. The device of claim 1, wherein the device is configured so that a dissipation of the produced RF power is 85-95% in the plasma gas discharge and 5-15% to the surface of the biological tissue.

5. The device of claim 1, the device is configured so that when the device electrode is several centimeters from the surface of the biological tissue a real dimension of a surface of biological tissue interacting with an RF field of the RF power is between 20 and 40cm$^2$.

6. The device of claim 1, wherein the device is configured so that before the ignition of the gas flow, 80-90% of incident power from the RF power generator is reflected by the biological tissue surface and during an operation stage of the device between 2and 4% of the incident power is reflected by the biological tissue surface.

7. The device of claim 1, wherein the device is configured to operate to provide a very low current density having a peak current density between 100 and 700 mA/cm$^2$ and an average value of between 10 and 200 mA/cm$^2$.

* * * * *